United States Patent [19]

Pfleger

[11] 4,041,763
[45] Aug. 16, 1977

[54] METHOD AND APPARATUS FOR AUTOMATICALLY SAMPLING MATERIAL IN PRE-PROGRAMMED POSITIONS

[76] Inventor: Frederick W. Pfleger, F. P. Developments, Inc., 27 Cherry Ave., Maple Shade, N.J. 08052

[21] Appl. No.: 657,017

[22] Filed: Feb. 10, 1976

[51] Int. Cl.² .............................................. G01N 1/10
[52] U.S. Cl. .................................................. 73/423 A
[58] Field of Search ...................... 73/423 A; 141/130; 23/259

[56] References Cited

U.S. PATENT DOCUMENTS

| | | | |
|---|---|---|---|
| 3,143,393 | 8/1964 | Des Hons | 23/253 |
| 3,168,124 | 2/1965 | Lenkey | 141/130 |
| 3,687,632 | 8/1972 | Natelson | 141/130 |

*Primary Examiner*—S. Clement Swisher
*Attorney, Agent, or Firm*—Seidel, Gonda & Goldhammer

[57] ABSTRACT

Material is inspected, transferred or sampled at one or more preselected positions in a rectangular array of columns and rows according to a predetermined program. A transfer tube, probe, or other element, referred to generally as a sampling element, is transported along predetermined rows of the array from the first to the last column position. When the sampling element reaches a preselected position at which material is to be inspected or transferred, the sampling element is actuated. For example, the sampling element is transported from a non-sampling position to a sampling position at which material can be inspected in or transferred to or from a container at the preselected position. The sampling element is then transported to the next position in the row at which material is to be inspected or transferred. After the sampling element reaches the last column of the last row, it is transported back to the first column of the array.

23 Claims, 15 Drawing Figures

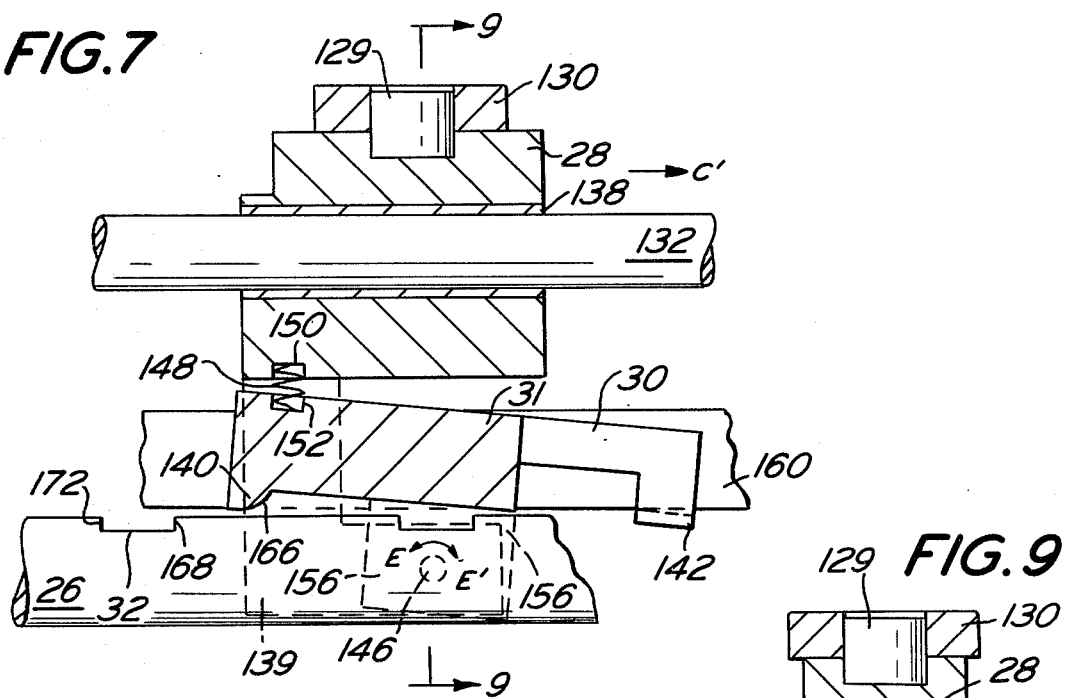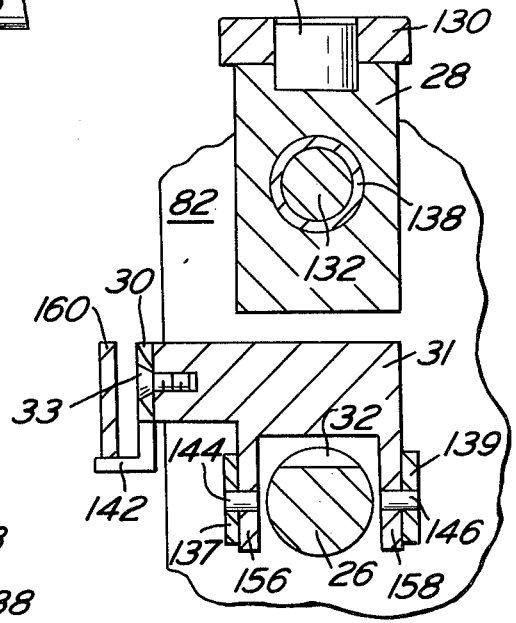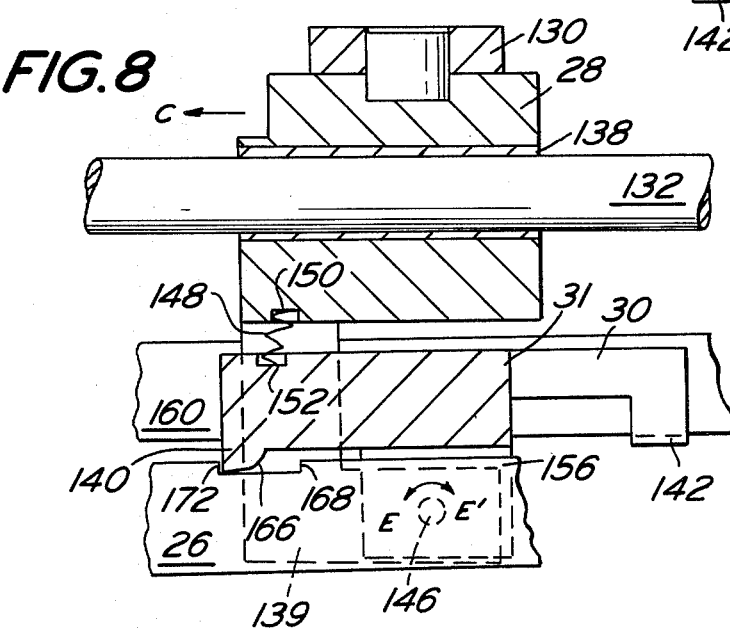

METHOD AND APPARATUS FOR AUTOMATICALLY SAMPLING MATERIAL IN PRE-PROGRAMMED POSITIONS

BACKGROUND OF THE INVENTION

The present invention relates to a method and apparatus for inspecting or transferring material at preselected positions in a rectangular array of rows and columns. In particular, the present invention is directed to a method and apparatus for automatically inspecting or transferring material at one or more preselected positions in a rectangular array by scanning every row of the array in the same direction.

Various machines are known in the art for automatically sampling the contents of a plurality of containers arranged in a rectangular array. In general, the machines can be distinguished by the particular patterns which they trace in scanning the containers. The more complex the pattern traced by the machine during a scan of the container array, the more complex the mechanical structure of the machine.

The most common type of pattern used to scan a rectangular array of containers is the boustrophedon pattern. More particularly, a transfer tube, probe, or other element for inspecting or transferring material, hereinafter referred to generally as a "sampling element" for ease of reference, is transported across adjacent rows of containers in opposite directions. A machine which traces this type of pattern while scanning an array of containers is described in U.S. Pat. No. 3,205,921 entitled Liquid Fraction Collecting Apparatus issued to Packard et al. In this patent, the sampling element is transported in a stepped boustrophedon pattern wherein the sampling element is stopped at every column position in a row. Two stepping motors are required to drive associated pulleys and cables to transport the sampling element in predetermined increments along the columns and rows of the container array.

The deficiencies in scanning an array of containers by predetermined increments in a boustrophedon pattern are three-fold. First, there may be containers in the array which are empty or which contain materials which cannot be sampled until a later time. Obviously, it is desirable to pass over these containers and pause to sample only those containers containing material ready for sampling. If the sampling element is transported in predetermined increments and caused to stop at each column position in each row of the container array, a considerable portion of time can be wasted in examining empty containers or containers which hold material not ready for sampling. Second, to drive the sampling element from row to row in a boustrophedon pattern requires two separate motors, one for driving the sampling element from the first column position of a row to the last column position, and the other motor for driving the element from the last position in the latter row to the last position in the next adjacent row. The operation of the motors is complex since they must work in synchronization with a plurality of intricate indexing mechanisms. Third, a machine which operates in the boustrophedon pattern requires bidirectional controls, increasing the possibility of machine malfunction.

Scanning patterns other than the boustrophedon pattern are also well-known in the art. For example, in U.S. Pat. No. 3,168,124 entitled Fraction Collector issued to Lenkey, there is described a machine for sampling the contents of containers arranged in a rectangular array by transporting the sampling element in predetermined increments across each column in the array. When the sampling element reaches the last container in a column, it flies back to the first container in the same column and advances to the next column in the array. The sampling element must pause at each container in the column, whether or not the container is empty or contains material not ready to be sampled. In the extreme, entire columns of the container array may include no containers having contents ready for sampling. Nonetheless, the sampling element must stop at each container. Considerable amounts of time can be wasted by transporting the sampling element in predetermined increments regardless of the state of the contents of the containers.

It is also known in the art to automatically scan one or more preselected containers in a rectangular array. For example, U.S. Pat. No. 3,143,393 entitled Apparatus for Automatically Performing Chemical Operations and Similar or Related Operations issued to des Hons, describes a machine for automatically sampling containers at preselected orthogonal coordinates of an array. Two separate motors are required to drive the probe to scan the array of containers. Furthermore, to enable automatic operation of the machine, the machine must be electrically preset by means of relays, and the two motors must be mechanically connected to contact arms and camming wheels which operate in synchronism. The contact arms and camming wheels are connected, through gearing, to the motor shaft, forming an elaborate mechanism.

A primary advantage of the present invention is to automatically inspect or transfer material at one or more preselected positions in a rectangular array.

A further advantage of the present invention is to provide a simple mechanical means for preselecting those positions in the array at which material is to be inspected or transferred.

Another advantage of the present invention is to automatically scan a rectangular array of positions without allocating machine time to examining positions in the array at which material is not to be inspected or transferred.

A still further advantage of the present invention is to automatically scan predetermined rows of the array in one direction only, and to advance from row to row without scanning a row more than once.

Yet another advantage of the present invention is to provide a relatively simple and efficient control mechanism for transporting a sampling element along a row of the array without pausing at positions in the row which are not ready for sampling and without separate directional controls.

BRIEF SUMMARY OF THE INVENTION

A sampling element for inspecting or transferring material is automatically transported across positions in a rectangular array of rows and columns according to a predetermined program. The sampling element is transported in the same direction along predetermined rows of the array. The sampling element is stopped at preselected column positions along a row, corresponding to the positions at which material is to be inspected or transferred. At each of the preselected positions, the sampling element is activated. When the sampling element is activated, material is inspected at or transferred to or from the preselected position for a predetermined interval of time. The sampling element is then transported to the next preselected position at which material is to be inspected or transferred. Power is automatically cut off to terminate movement of the sampling element when the entire array has been scanned according to the program.

BRIEF DESCRIPTION OF THE DRAWINGS

FIG. 7 is a partial view in cross-section taken along the lines 7—7 in FIG. 2 showing the operational state of the apparatus in FIG. 2 during a scan of a row in the array.

FIG. 8 is a partial view in cross-section taken along the lines 7—7 in FIG. 2 showing the operational state of the apparatus in FIG. 2 between consecutive scans of predetermined rows in the array.

FIG. 9 is a view in cross-section taken along the lines 9—9 in FIG. 7.

FIG. 10 is a view in cross-section taken along the lines 10—10 in FIG. 4.

Figure 1:
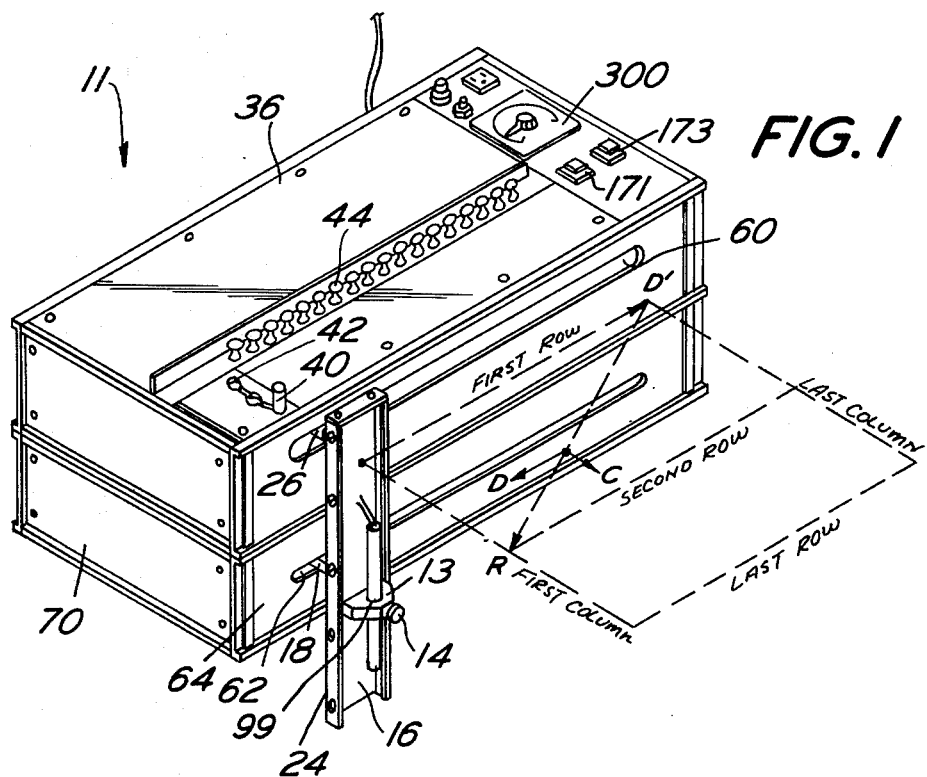
FIG. 1 is a view in perspective of an apparatus for automatically inspecting or transferring material to or from preselected positions in a rectangular array.

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Referring to the drawings in detail wherein like numerals indicate like elements, FIG. 1 is a view in perspective of an apparatus for inspecting or transferring material at one or more preselected positions in a rectangular array (shown by dashed lines), constructed according to the principles of the present invention and designated generally as 11. A holder 13 houses a sampling element 99 which is intended to represent a transfer tube, probe, or other element for inspecting or conducting material. The structure of holder 13 is more clearly shown in FIG. 4. A threaded passage 15 extends laterally within holder 13 and intersects passage 12. The sampling element is inserted in passage 12 and a screw 14 is advanced in threaded passage 15 to prevent the element from sliding in passage 12 during operation of the apparatus.

Holder 13 is connected to a plate 16 by means of a screw 17, FIG. 4, so that holder 13 moves with plate 16 when plate 16 is driven reciprocally by shaft 18, as will be explained more fully hereinafter. Plate 16 is slidably mounted in a frame 24, FIG. 10, and is mechanically coupled to shaft 18 by means of a rack 20 and gear 22. Rack 20 is fastened to plate 16 and is meshed with gear 22 so that rotary motion of gear 22 in the directions indicated by arrows A and A' in FIG. 10 causes translational motion of plate 16 in the direction of arrows B and B'. Gear 22 is located within frame 24 and is coupled to shaft 18 which passes through an aperture 19 in frame 24. Gear 22 is protected by a retaining plate 210 which is connected to frame 24 by means of screws 211, 213, 215 and 217. Frame 24 confines the translational motion of rack 20 and plate 16, due to rotation of gear 22, to the linear paths indicated by arrows B and B'.

Figure 4:
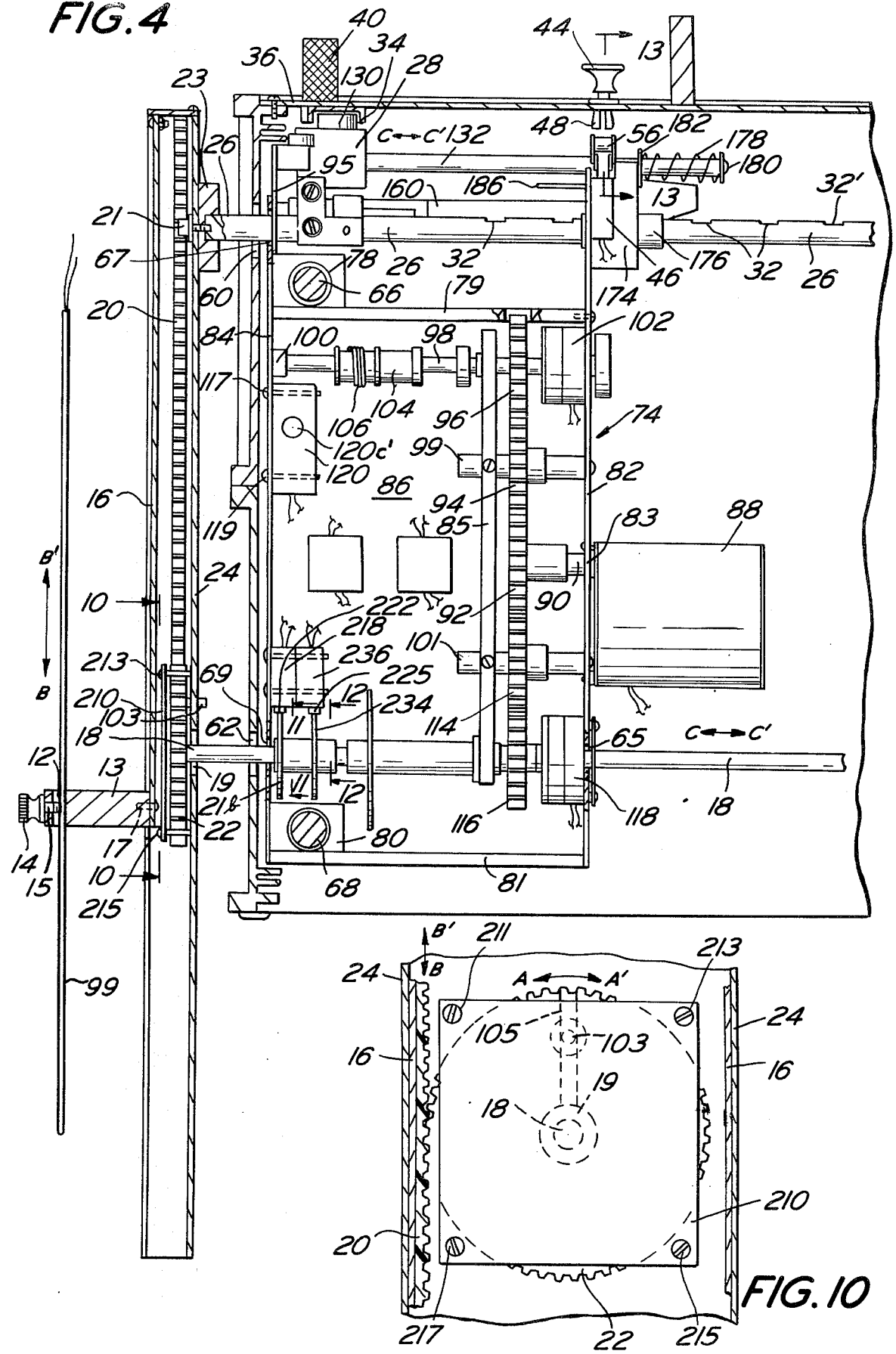
FIG. 4 is a view in cross-section taken along the lines 4—4 in FIG. 2.

Referring to FIG. 4, frame 24 is fastened to a rod 26 by means of a screw 21 and ring 23 in which rod 26 is seated. Rod 26, and therefore frame 24, is driven in preselected increments along a path, indicated by the arrow C, by a block 28 having a member 31, FIGS. 7 and 8, which intermittently contacts notches 32 in rod 26. The method by which block 28 drives rod 26 along path C will be described in further detail below.

Figure 2:
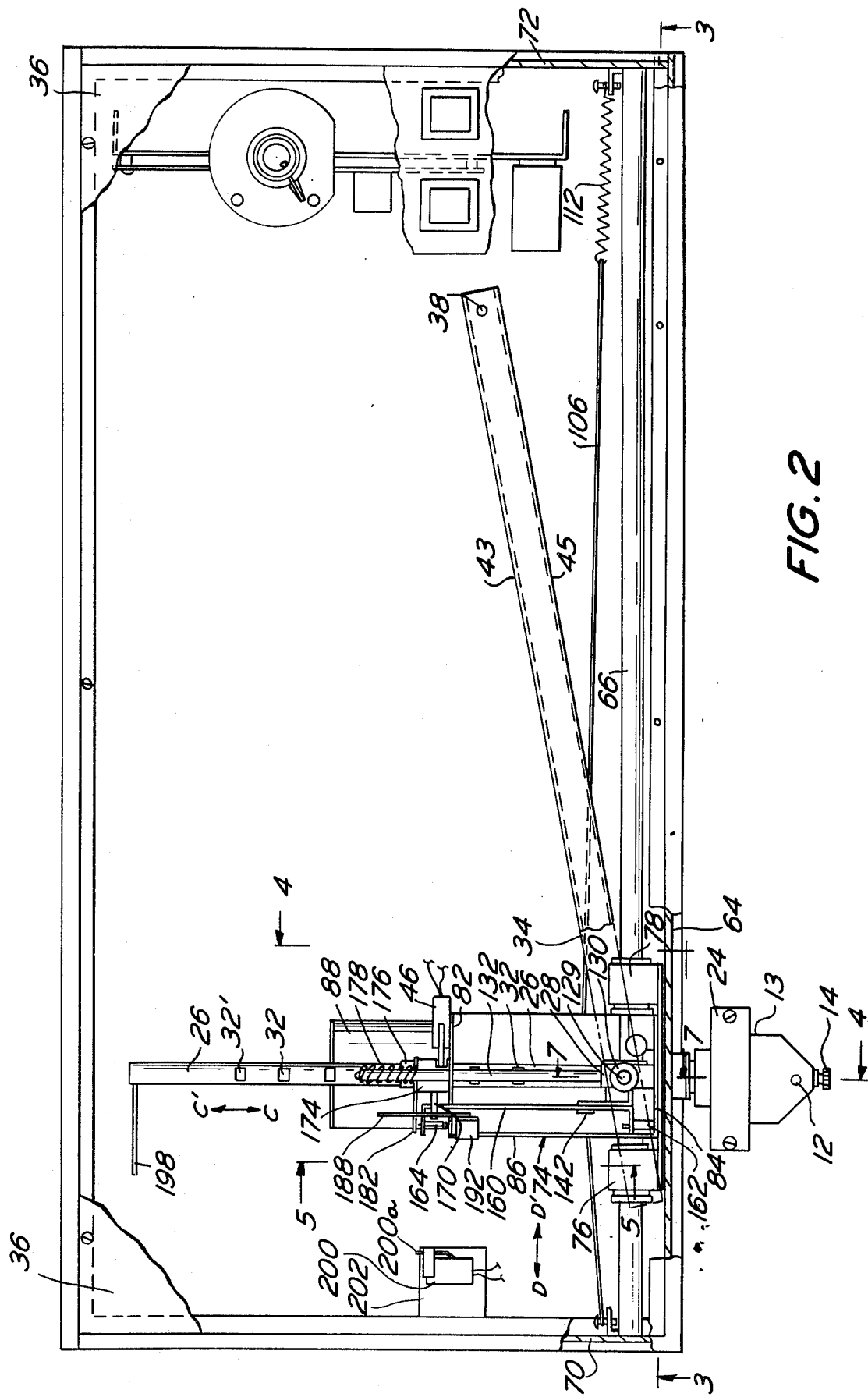
FIG. 2 is a top plan view of the apparatus shown in FIG. 1, with a portion of the apparatus cut away.

Block 28 drives rod 26 along path C in cooperation with guide rail 34, FIG. 2. Guide rail 34 is pivotally attached to the underside of a top casing member 36 at pivot 38. In particular, guide rail 34 is provided with a flanged portion 214, FIG. 3, which fits between top casing member 36 and a lip 212 fastened thereto. A handle 40 having a threaded shaft 41 which passes through a slot 42 in top casing member 36 is advanced in a threaded passage (not shown) in flanged portion 214 to lock guide rail 34 in place once guide rail 34 has been rotated to the desired position. As will be described more fully hereinafter, the position of handle 40 in slot 42 determines the size of the incremental displacement of rod 26 in the direction C.

Referring to FIG. 4, both rod 26 and shaft 18 are slidably mounted on a carriage 74. Carriage 74 moves reciprocally in the directions indicated by arrows D and D', FIG. 2, as will be explained more fully below. Rod 26 and shaft 18 pass through slots 60 and 62, respectively, in a front casing member 64, FIG. 4. Slots 60 and 62 extend in the directions D and D', FIG. 1. Thus, as carriage 74 moves in the directions D and D', it transports rod 26 and shaft 18 in the same directions. As carriage 74 moves in the direction D', a roller 56, in a program switch 46, FIG. 13, which is fastened to carriage 74, FIG. 4, contacts one or more depressed cams 44. The depressed cams 44 are located at preselected column positions at which material is to be inspected or transferred according to the scanning program. Program switch 46 serves to stop carriage 74 along path D' when roller 56 contacts a depressed cam 44. If a cam 44 is not depressed, roller 56 will not contact it and carriage 74 will not stop. While carriage 74 is stopped, material is inspected or transferred at the preselected position for a predetermined interval of time. As will be explained in further detail hereinafter, those cams 44 which are depressed operate program switch 46 only when carriage 74 travels in the direction D'. When carriage 74 travels in the reverse direction, direction D, cams 44 do not actuate program switch 46.

Figure 13:
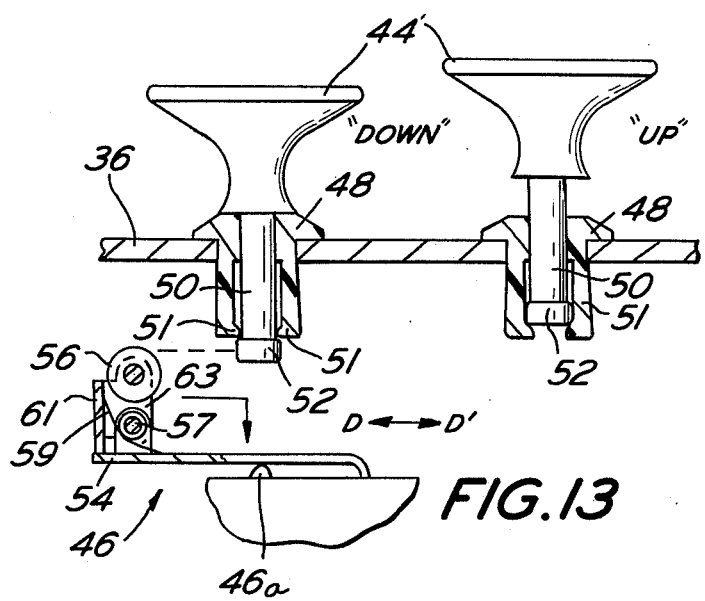
FIG. 13 is a view in cross-section taken along the lines 13—13 in FIG. 4.

In the preferred embodiment of the invention shown in FIG. 13, each cam 44 is slidably mounted in a bushing 48 fastened to top casing member 36. Cam 44 is provided with a shaft 50 having an annular head 52. Bushing 58 is provided with a plurality of flexible flanges legs 51 for controlling the position of annular head 52. When cam 44 is in the "UP" position, FIG. 13, flanged legs 51 prevent annular head 52 from dropping downwardly and being contacted by roller 56. On the other hand, when cam 44 is depressed downwardly past legs 51, the "DOWN" position, legs 51 prevent head 52 from being pushed upwardly into the "UP" position by roller 56.

Program switch 46 is a commercially available unit in which roller 56 is rollably mounted on a pivotable member 63 which is pivotally connected to a leaf spring 54 at a pivot 57. Pivotable member 63 includes a wall 61, shown resting in the vertical position against leaf spring 54 prior to contact of head 52 by roller 56. A spring 59 is wound around pivot 57. One end of spring 59 presses against the wall 61, and the other end of spring 59 presses against leaf spring 54, thereby biasing wall 61 in the vertical portion against leaf spring 54. Program switch 46 is positioned on carriage 74 so that, when roller 56 contacts annular head 52 as carriage 74 travels in the direction D', member 63 cannot rotate about pivot 57 because wall 61 presses against leaf spring 54. Thus, leaf spring 54 moves downwardly under the contacting force of head 52 on roller 56 to operate actuator 46a, causing carriage 74 to stop, as will be described in greater detail below with respect to the electrical schematic shown in FIGS. 14A and B. When, however, roller 56 contacts annular head 52 as carriage 74 travels in the direction indicated by arrow D, member 63 pivots about pivot 57 against the force of spring 59 and leaf spring 54 does not contact actuator 46a. Program switch 46, then, only stops carriage 74 as the carriage traverses a path in the direction of arrow D'.

Figure 3:
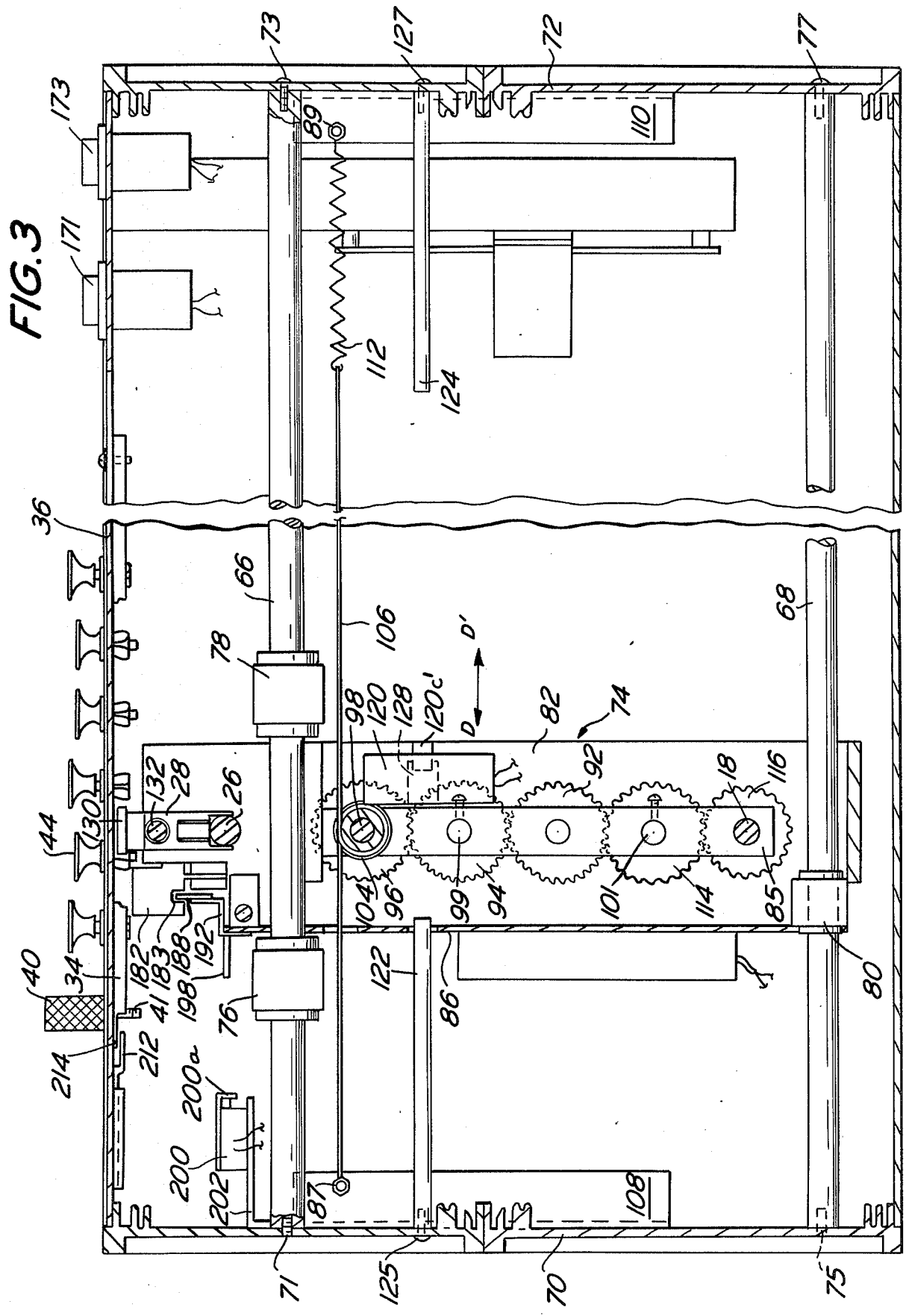
FIG. 3 is a view in cross-section taken along the lines 3—3 in FIG. 2.

Referring to FIG. 3, a pair of parallel rods 66 and 68 are connected to side casing members 70 and 72 by screws 71, 73, 75 and 77. The longitudinal axes of rods 66 and 68 extend in the directions D and D'. A pair of bushings 76 and 78 are fastened to top carriage member 79 and front carriage member 84 of carriage 74, FIG. 4. In addition, a bushing 80 is fastened to bottom carriage member 81 and front carriage member 84. Bushings 76, 78 and 80 are slidably mounted on rods 66 and 68, FIG. 3, permitting carriage 74 to slide along rods 66 and 68 in the directions D and D'.

A motor 88, FIG. 4, having a drive shaft 90 which is rotatable in two directions is fastened to the backside of rear carriage member 82. Rear carriage member 82 has an aperture 83 through which drive shaft 90 passes. Drive shaft 90 extends laterally towards front casing member 84 and is connected to a main gear 92 which is disposed within carriage 74 between rear carriage member 82 and a strut 85. Strut 85 supports shafts 98 and 18. Main gear 92 is connected through an idler gear 94 to a gear 96. Idler gear 94 is rotatably mounted on post 99 which is fastened to strut 85. Gear 96 is removably coupled by an electrically operated clutch 102 to a shaft 98 which is rotatably mounted in a bearing 100 fastened to front carriage member 84.

Shaft 98 is provided with a cylindrical drum 104 located between bearing 100 and strut 85. A cable 106 is wrapped around drum 104 and is anchored by nuts 87 and 89 to brackets 108 and 110, FIG. 3. Brackets 108 and 110 are fastened to side casing members 70 and 72. In the preferred embodiment shown in FIG. 3, cable 106 is anchored in bracket 110 by means of a spring 112 which provides tension in the cable. As drum 104 rotates with shaft 98, it traverses the length of cable 106, causing carriage 74 to slide along shafts 66 and 68 in the directions D or D'.

Main gear 92, FIG. 4, is also connected to a gear 116 through an idler gear 114 rotatably mounted on post 101 which is fastened to strut 85. Gear 116 is removably coupled to shaft 18 by an electrically operated clutch 118. Shaft 18 is rotatably and slidably mounted in carriage 74 through aperture 69 in front carriage member 84 and aperture 65 in rear carriage member 82. Also, as mentioned previously, shaft 18 is coupled to gear 22 which meshes with rack 20 in frame 24. When clutch 118 couples gear 116 to shaft 18, gear 22 drives rack 20 reciprocally in the direction of arrows B or B' depending on the direction of rotation of drive shaft 90.

A switch 120 for reversing the direction of rotation of drive shaft 90 is fastened to the backside of front carriage member 84 by screws 117 and 119, FIG. 4. Switch 120 is positioned to contact laterally extending rods 122 and 124, FIG. 3, which are fastened to side casing members 70 and 72 by screws 125 and 127. Switch 120 is provided with a passage 128 and a slidable actuator 120c' which slides reciprocally in passage 128 when it contacts rods 122 and 124. As will be described more fully below, switch 120 is electrically connected to motor 88 and, upon contacting rods 122 and 124, actuator 120c' causes the direction of rotation of drive shaft 90 to reverse. Thus, with gear 96 coupled to shaft 98 by means of clutch 102, carriage 74 alternately reverses direction between arrows D and D' when actuator 120c' is alternately displaced by rods 122 and 124. For example, when drum 104 drives carriage 74 and frame 24 through a complete scan of the first row in the array in the direction D', rod 124 operates switch 120 which causes shaft 90 to reverse its direction of rotation. As a result, drum 104 drives carriage 74 back to its initial column position in the direction D. When carriage 74 reaches its initial column position, rod 122 operates switch 120, causing shaft 90 to again reverse its direction of rotation. Drum 104, then, drives carriage 74 back towards rod 124 in the direction D'. Each time carriage 74 travels from rod 122 to rod 124, frame 24 scans a new row in the array.

Referring to FIG. 4, block 28 is slidably mounted on a rod 132 disposed above and parallel to rod 26. Rod 26 is securely fastened to a plate 94 which is fastened to the backside of front carriage member 84. Block 28 is provided with a circular projection 129, FIG. 2. A roller 130 is seated on block 28 around projection 129. In particular, roller 130 is seated on block 28 to fit between and rollably contact flanges 43 and 45 of guide rail 34. Therefore, as carriage 74 slides reciprocally in the directions D and D', block 28 slides reciprocally along guide rail 34 and rod 132. Specifically, block 28 slides reciprocally along rod 132 in the directions C and C'. As carriage 74 travels in the direction D', towards the last column in the array during a scan of a row, block 28 travels in the direction C' along rod 132; and as carriage 74 returns to the first column in the array, traveling in the direction D, block 28 travels along rod 132 in the direction C.

As block 28 slides over rod 26 in the direction C', it does not drive rod 26, but as the block slides in the direction C it drives rod 26 in the same direction, as will be explained more fully below. More particularly, as guide rail 34 guides block 28 along shaft 132 in the direction C, block 28 lodges in one of the notches 32 in rod 26 and drives or displaces rod 26 in the direction C. Block 28, however, does not lodge in notches 32 of rod 26 when it travels along rod 132 in the direction C'. When traveling in the direction C', block 28 slides over rod 26 without displacing the rod.

As mentioned previously, rod 26 is fastened to frame 24, FIG. 4. In addition, rod 26 is slidably mounted in carriage 74 through an aperture 67 in front carriage member 84 and a bushing 176 securely mounted in rear carriage member 82. Also, as already mentioned, gear 22 is meshed with rack 20 and is coupled to shaft 18 which is both rotatably and slidably mounted in apertures 69 and 65 in front and rear carriage members 84 and 82. Therefore, when block 28 drives rod 26 in the direction C, shaft 18 slides in the direction C as well. Frame 24, then, also travels in the direction C.

In view of the foregoing, when carriage 74 returns to the first column in the array in the direction D, frame 24 travels simultaneously in the directions C and D, FIG. 1. The net motion of frame 24, therefore, is in the direction R as carriage 74 returns to the first column in the array. Direction R is oblique with respect to directions D and C. When carriage 74 returns to the first column position in the array, therefore, frame 24 also returns to the first column position but it advances in the direction C to the next row to be scanned. On the other hand, as already mentioned, as carriage 74 travels in the direction D' during a scan of a row, block 28 slides along rod 132 without engaging any of the notches 32 in rod 26. As a result, when frame 24 travels in the direction D', it is not displaced in the direction C. Thus, alternating motion of carriage 74 in the directions D' and D causes frame 24 to alternately scan a row in the direction D' and advance in the direction R to the first column position in the next row to be scanned.

Figure 5:
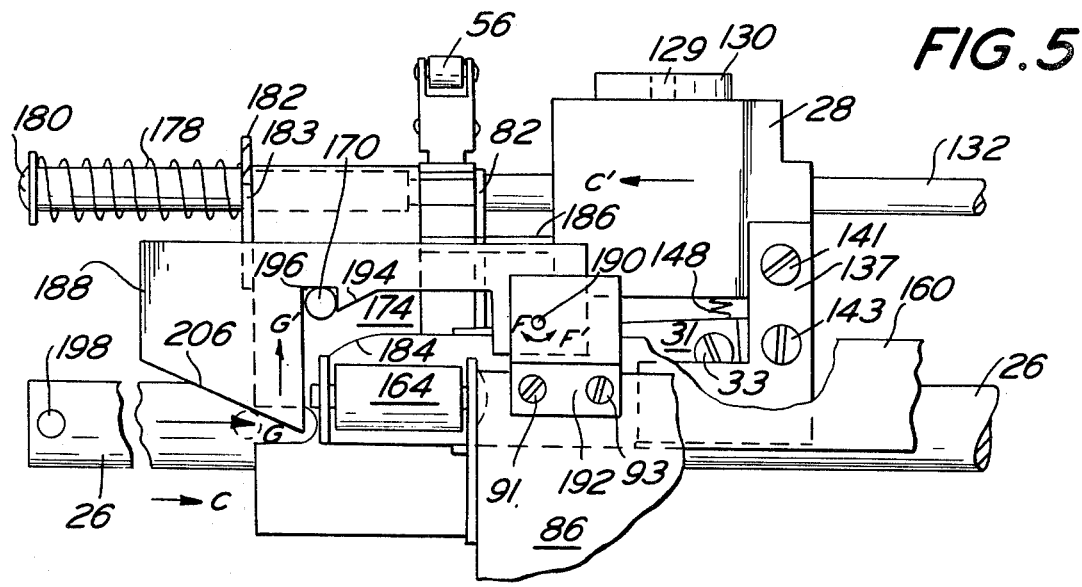
FIG. 5 is a view in cross-section taken along the lines 5—5 in FIG. 3 showing a portion of the apparatus in FIG. 2 in its operating state after the first row of the array has been scanned.

The structure of block 28 and the interrelationship between block 28 and rod 26 is more clearly shown in FIGS. 5–9. Block 28 is provided with a passage 138, FIG. 7, for slidably contacting shaft 132. A left L-shaped member 137, FIG. 5, is fastened to block 28 by screws 141 and 143. A right L-shaped member 139 is similarly fastened to block 28 and is shown in partial cross-section in FIG. 9. A pivotable member 31, FIG. 9, straddles rod 26 and is pivotally mounted on L-shaped members 137 and 139 by means of pivots 144 and 146. Pivotable member 31 is provided with a finger 140, FIGS. 7 and 8, for engaging notches 32 in rod 26. A member 30 having a flange 142, FIG. 9, is fastened to member 31 by a screw 33. The operation of finger 140 and flange 142 is discussed more fully below. Member 31 is also connected to a spring 148 which fits in a recess 150 in block 28, FIGS. 7 and 8, and a recess 152 in member 31. Spring 148 provides a biasing force which urges member 31 to rotate about pivots 144 and 146 in the direction E, FIGS. 7 and 8. When member 31 rotates in the direction E, finger 140 lodges in notch 32, FIG. 8. As block 28 slides along rod 132 in the direction C, with finger 140 lodged in notch 32, finger 140 contacts notch wall 172 and drives rod 26 in the direction C. By contrast, as shown in FIG. 7, when block 28 slides along rod 132 in the direction C', finger 140 slides over notch wall 68 without lodging in notch 32.

Referring to FIG. 9, legs 156 and 158 of member 31 straddle shaft 26. A register plate 160 is positioned in proximity to member 30 and rests on flange 142. Register plate 160 is rotatably mounted on carriage 74 by means of a pivot 162, FIG. 2, connected to front carriage member 84 and a pivot 164 connected to rear carriage member 82. Register plate 160 rotates about pivots 162 and 164 and presses against flange 142, FIG. 7. Register plate 160 urges member 31 to rotate about pivots 144 and 146 in the direction E', FIG. 7, opposite to the direction of rotation caused by spring 148.

In the preferred embodiment shown in FIGS. 7–9, the rotational force produced about pivots 144 and 146 by spring 148 exceeds the rotational force produced about the pivots by register plate 160 when it rests on flange 142. Therefore, unless a further rotational force can be produced to offset the rotational force provided by spring 148, member 31 will rotate in the direction E and finger 140 will lodge in notch 32, FIG. 8. With finger 140 lodged in notch 32, as block 28 slides along rod 132 in the direction C, finger 140 presses against notch wall 172, driving rod 26 in the direction C. As already mentioned, as carriage 74 travels in the direction D to return to the first column position in the array, FIG. 2, guide rail 34 causes block 28 to travel along rod 132 in the direction C. Thus, as carriage 74 returns to the first column position, finger 140 drives rod 26 in the direction C. Accordingly, frame 24, which is fastened to rod 26, simultaneously moves in the directions D and C. That is, frame 24 travels along the oblique path R to the first column of the next row to be scanned, FIG. 1.

Referring to FIGS. 7 and 8, finger 140 is provided with a rounded or tapered edge 166. As carriage 74 travels in the direction D' during the scan of a row, block 28 slides along rod 132 in the direction C', and tapered edge 166 contacts notch wall 168 and slides over wall 168 to contact the exterior surface of rod 26. Further movement of block 28 in the direction C' causes tapered edge 166 to slide along the exterior surface of rod 26 towards the next notch 32. As taperted edge 166 slides over wall 168, wall 168 urges member 31 upwards against the biasing force provided by spring 148. Consequently, member 31 rotates in the direction E', FIG. 7. Tapered edge 166 is assisted in sliding over wall 168, against the biasing force provided by spring 148, by the moment produced by register plate 160 resting on flange 142. Thus, as carriage 74 travels towards the last column in a row in the direction D', finger 140 does not lodge in a notch 32 and does not displace rod 26. Frame 24, therefore, is not affected by the motion of block 28 in the direction C' and the frame travels with carriage 74 in the direction D' to the last column of the row being scanned, FIG. 1.

Prior to automatic operation of the machine, holder 13 must be aligned with the first column of the first row of containers to be scanned. To align holder 13 prior to the first scan, rod 26 must freely slide between front and rear carriage members 84 and 82 while block 28 is stationary. Finger 140, therefore, must be prevented from pressing against notch wall 172 as rod 26 is displaced in the direction C'. For this purpose, a rod 170 fastened to a rear block 174, FIG. 2, depresses register plate 160 against flange 142 prior to automatic operation, FIG. 6. The additional moment produced by rod 170 causes finger 31 to rotate in the direction E' away from rod 26, FIG. 7. Therefore, as rod 26 moves in the directin C' with block 28 stationary, wall 172 in notch 32 cannot contact finger 140 and rod 26 can freely slide through front and rear carriage members 84 and 82. Thus, prior to automatic operation of the machine, holder 13 can be aligned with the first row of containers to be scanned by sliding rod 26 until holder 13 reaches the desired row position.

More specifically, to prevent finger 140 from contacting wall 172 of notch 32 prior to automatic operation of the apparatus, rear block 174 is positioned behind rear carriage member 82, FIG. 4, and is slidably mounted on bushing 176 mounted in an aperture (not shown) in rear carriage member 82. Rod 26 is slidably mounted in bushing 176. A spring 178 is mounted axially on rod 132, FIG. 4, and is anchored to one end of rod 132 by a screw 180. Spring 178 contacts a plate 182, FIG. 2, fastened to the rear surface of block 174 and urges block 174 along busing 176 towards rear carriage member 82. When block 174 is pushed against rear carriage member 82 by spring 178, FIG. 6, rod 170 depresses register plate 160 against flange 142, causing member 31 to rotate in the direction E', FIG. 7, against the moment produced by spring 148. The urging force of rod 170 against register plate 160, then, causes member 31 to rotate such that finger 140 is displaced upwardly and away from contact with shaft 26. Consequently, shaft 26 can slide without obstruction through front and rear carriage members 84 and 82, and holder 13 can be brought into registration with the first row to be scanned.

As mentioned previously, during automatic operation of the apparatus, as carriage 74 returns to the first column position in the direction D, finger 140 must lodge in notch 32 and press against wall 172 to drive shaft 26 in the direction C. However, prior to automatic operation of the apparatus, to align frame 24 with the first row of containers to be scanned, rod 170 depresses register plate 160 to bias finger 140 away from rod 26. Unless the biasing force provided by rod 170 is eliminated or overcome during automatic operation of the apparatus, finger 140 will remain biased away from rod 26 and the rod will not be driven in the direction C. That is, as carriage 74 returns to the first column position, frame 24 will not advance to the next row to be scanned. Therefore, to eliminate the biasing force provided by rod 170, register plate 160 is provided with a downwardly sloping surface 184, FIGS. 5 and 6, so that rod 170 releases from contact with the register plate when lock 174 slides in the direction C' on bushing 176.

To enable block 174 to be displaced in the direction C' during automatic operation, block 174 is provided with a rod 186, FIG. 4, extending laterally therefrom towards block 28. In addition, rear carriage member 82 is provided with an aperture (not shown) through which rod 186 is slidably mounted. When carriage 74 travels in the direction D' during the scan of the first row of containers, guide rail 34 guides block 28 towards rear carriage member 82 along rod 132 in the direction C'. As block 28 slides along rod 132 in the direction C', it contacts rod 186 and urges block 174 backwards along bushing 176 in the direction C against the biasing force of spring 178. As block 174 moves backward along bushing 176, FIG. 2, rod 170 reaches the downwardly sloping surface 184 of register plate 160, FIGS. 5 and 6, and releases from contact with the register plate. The biasing force provided by spring 148, FIGS. 7 and 8, now causes member 31 to rotate in the direction E. Therefore, as carriage 74 returns to the first column position in the direction D, finger 140 contacts notch wall 172, causing rod 26 to be driven in the direction C. Rod 26 is driven in the direction C as carriage 74 travels in the direction D since rod 170 releases from contact with register plate 160 when carriage 74 reaches the last column in the first row scanned.

Figure 6:
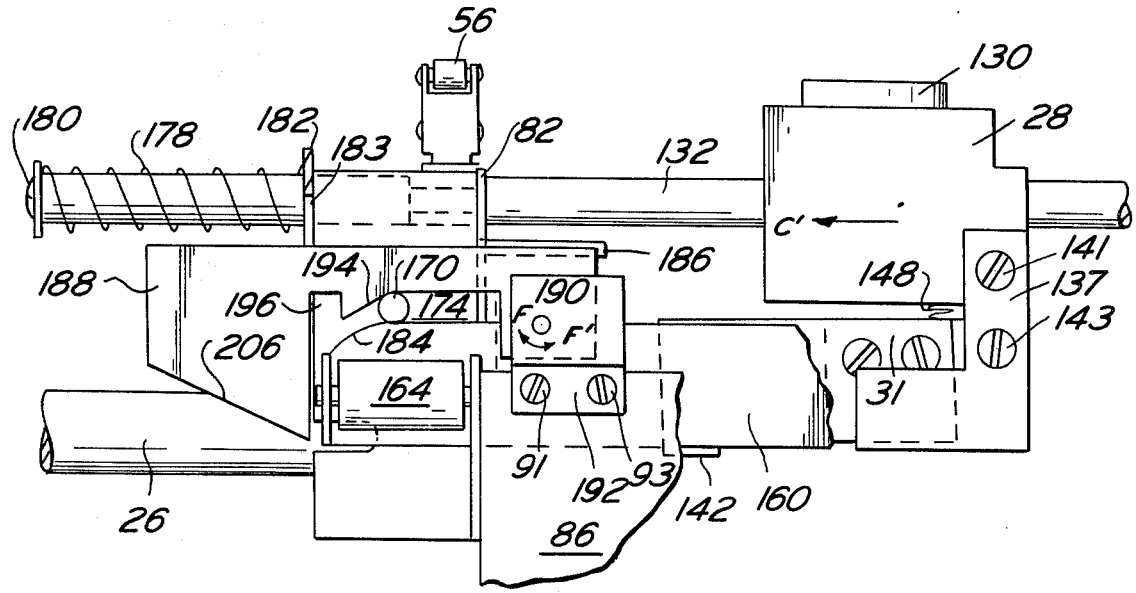
FIG. 6 is a view in cross-section taken along the lines 5—5 in FIG. 2 showing the apparatus in FIG. 2 in its operating state prior to completion of the first scan of the first row in the array.

To keep rod 170 biased away from contact with register plate 160 as carriage 74 travels in the direction D, a latch 188 is pivotally mounted, at pivot 190, to an angle bracket 192 fastened to side carriage member 86 by screws 91 and 93, FIGS. 5 and 6. Latch 188 is positioned parallel to rod 26 and passes through a notch 183 in plate 182, FIG. 3, which permits latch 188 to rotate in the directions F and F', FIGS. 5 and 6. Latch 188 is provided with a camming surface 194 and a notch 196. As carriage 74 moves in the direction D' during the scan of the first row, block 28 urges block 174 against spring 178 and rod 170 slidably contacts camming surface 194, causing latch 188 to rotate in the direction F, FIG. 5. As carriage 74 continues to move in the direction D', block 28 continues to urge block 174 backwards along bushing 176 and rod 170 continues to slide along camming surface 194. Therefore, when carriage 74 reaches the last column in the first row, rod 170 is caused to release from contact with camming surface 194 and to enter notch 196, FIG. 5. As rod 170 enters notch 196, latch 188 rotates under its own weight in the direction F', locking rod 170 in notch 196. Notch 196, then, prevents block 174 from traveling along bushing 176 towards rear carriage member 82 under the biasing force of spring 178, thereby preventing rod 170 from contacting register plate 160.

More particularly, latch 188 is positioned relative to register plate 160 so that notch 196 is in juxtaposition with downwardly sloping surface 184 of register plate 160. Therefore, once carriage 74 reaches the last column in the first row of containers, notch 196 prevents rod 170 from depressing register plate 160 and causing finger 140 to rotate away from rod 26. Rod 170 remains locked in notch 196 until the array has been scanned according to the program and the machine has automatically terminated operation. With rod 170 locked in notch 196, spring 148 urges finger 140 into contact with rod 26, FIG. 8. Thus, whenever carriage 74 reverses direction, after reaching the last column of a row, and travels back towards the first column position, block 28 slides along rod 132 in the direction C and finger 140 presses against notch wall 172 to drive shaft 26 in the direction C.

As carriage 74 returns to the first column position in the direction D, shaft 26 must be driven the precise distance required to align frame 24 with the predetermined rows to the scanned. The distance which finger 140 displaces rod 26 depends upon the distance traversed by block 28 along rod 26. That distance, in turn, is determined by the initial positioning of block 28 on rod 26 since block 28 travels reciprocally between its initial position and rear carriage member 82 under constraint of guide rail 34. By way of example, depending on the initial position of block 28 on rod 26, the finger 140 can lodge in adjacent notches 32 in which case shaft 26 will be advanced to scan every row of the array. Alternatively, finger 140 can lodge in every second or third notch 32 along rod 26 in which case shaft 26 will be advanced to scan every second or third row of the array. The initial position of block 28 on rod 26 is fixed by the location of guide rail 34, FIG. 2. The position of guide rail 34 is adjusted by moving handle 40 in slot 42, FIG. 1, and is fixed by locking guide rail 34 into position prior to automatic operation of the apparatus.

As already explained, block 28 traverses rod 26 between its initial position and rear carriage member 82. In addition, shaft 26 is driven in the direction C as carriage 74 travels in the direction D. When the last row is scanned, it is desirable to return carriage 74 to the first column position and terminate automatic operation of the apparatus. For this purpose, rod 26 is provided with a rod 198, FIG. 2, for operating a switch 200. Rod 198 extends laterally from rod 26 towards side casing member 70. Switch 200 is mounted on an angle bracket 202 fastened to side casing member 70, FIG. 3, and is provided with an actuator 200a which faces rod 198. Rod 198 is positioned on rod 26 to depress actuator 200a when rod 26 has been fully extended in direction C and carriage 74 has scanned the last row and returned along path D to the first column position. Switch 200 is electrically connected to motor 88 so that, when actuator 200a is depressed by rod 198, switch 200 cuts off power to motor 88 and the apparatus ceases automatic operation.

Following a complete scan of the predetermined rows of the array, when rod 26 has been fully extended and carriage 74 has returned to the first column position, rod 198 operates switch 200 to cut off power to the machine as previously explained. However, unless finger 140 is dislodged from the last notch, designated as 32', FIG. 4, in rod 26, the rod cannot be pushed back in the direction C' to align frame 24 with the row in the array to be scanned next. To dislodge finger 140 from the last notch 32', latch 188 is provided with an inclined surface 206 behind notch 196, FIGS. 5 and 6. As shown by the arrows G and G', FIG. 5, as the last portion of rod 26 is driven in the direction C, rod 198 slidably contacts inclined surface 206 and causes latch 188 to move upwardly in the direction G'. As latch 188 moves in the direction G', notch 196 releases rod 170 and spring 178 pushes block 174 back towards rear carriage member 82. A block 174 approaches rear carriage member 82, rod 170 contacts register plate 160 and depresses the register plate against flange 142. Member 31, therefore, rotates in the direction E', as previously explained, causing finger 140 to rotate away from shaft 26. Consequently, with finger 140 disengaged from notch 32', FIG. 4, rod 26 can be freely moved in the direction C' to align frame 24 with the first row in the container array to be scanned next.

The preceding portion of the disclosure is directed primarily to the mechanical operation of the invention in response to the electrical controls provided by switches 46, 236, 218, 120 and 200. The sequence of electrical operations in controlling the mechanical steps described above will be described in detail hereinafter.

Figure 14A:
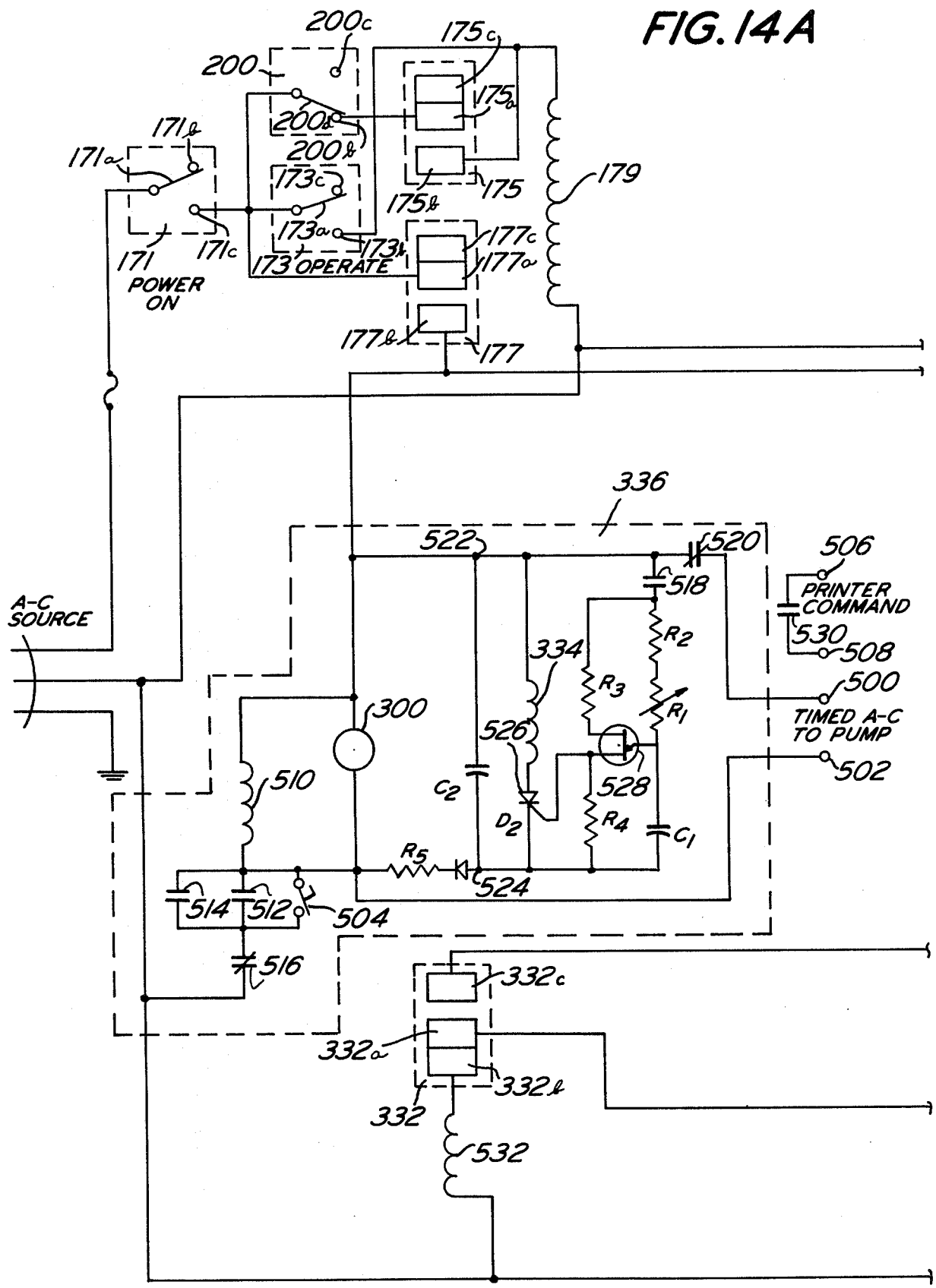
FIG. 14a and b comprise an electrical schematic of the electrical controls in the apparatus shown in FIGS. 1-4.

Referring to FIGS. 14A and B, there is shown the interconnection of switches 46, 236, 218, 120 and 200 with motor 88, clutches 102 and 118, switch 171, and switch 173. Switch 171, hereinafter referred to as "the power on" switch, is a conventional two-position single-throw switch. Movable contact 171a is connected to an ac source such as a conventional 115 volt line source. When power on switch 171 is operated, movable contact 171a connects with contact 171c to supply a current path to switch 173, designated hereinafter as "the operate switch". Operate switch 173 is a conventional momentary contact switch which is connected to contact 175. Power on switch 171 is also connected to momentary contact switch 200 which automatically terminates operation of the machine when all predetermined rows of the array have been scanned. In its normal position, movable contact 200a is in connection with contact 200b to supply a current path to movable contact 175a.

Prior to automatic operation of the apparatus, movable contact 171a makes connection with contact 171b, movable contact 173a makes connection with contact 173c, and movable contact 200a makes connection with contact 200b. When power on switch 171 is closed, that is, when movable contact 171a makes connection with contact 171c, no current flows through coil 179 and contacts 175a and 175c remain connected, as do contacts 177a and 177c.

To begin automatic operation of the machine, switch 173 is depressed, causing movable contact 173a to momentarily connect with contact 173b. As a result, current flows through contact 173b to coil 179. When energized, coil 179 causes movable contact 175a to make connection with contact 175b and movable contact 177a to make connection with contact 177b. Therefore, current flows through contact 177b energizing motor 88 and coil 309. When movable contact 173a re-connects with contact 173c, current continues to flow through contacts 200a and 200b to contacts 175a and 175b and coil 179, and coil 179 remains energized. Thus, further operation of switch 173 during automatic operation of the apparatus will have no effect on the current flow.

Secondary coil 311 in transformer 310 is connected to an a-c/d-c converter 312 which converts the alternating current impressed on the secondary coil to a d-c voltage across lines 314 and 316. Line 316 is connected to the movable contacts of switches 46, 236 and 218 and relay contact 318a. Switch 46 is hereinafter referred to as "the program switch"; switch 236 is referred to as "the top sensing switch"; and switch 218 is referred to as the bottom sensing switch. Line 314 is connected to clutches 102 and 118. Clutch 102 is hereinafter referred to as the left/right clutch, and clutch 118 is referred to as the up/down clutch. Line 314 is also connected to one side of coils 320, 322 and 324. The other side of coil 320 is connected to relay contact 338b and, through a diode, to contact 46b of program switch 46. The other side of coil 322 is connected to contact 218a in bottom sensing switch 218 and contact 120a in switch 120. Switch 120 is hereinafter referred to as the carriage direction switch. The other side of coil 324 is connected to relay contact 340b and movable contact 120c in carriage direction switch 120.

At the start of automatic operation of the apparatus, that is, when power on switch 171 and operate switch 173 are first depressed, movable contact 46a makes connection with contact 46c in program switch 46. Current, therefore, does not flow through coil 320. Coil 320 controls contacts 318 and 338. Therefore, movable contact 318a makes connection with contact 318c and movable contact 338a makes connection with contact 338c. Movable contact 236a, in top sensing switch 236, FIG. 2, is not yet operated and, therefore, makes connection with contact 236c. Therefore, contact 236 does not transmit the voltage on line 316, FIG. 14B, to contacts 340a and 338a. Contact 318c, however, is connected to line 316 through contact 318a and to left/right clutch 102 so that current flows through contacts 318a and 318c to clutch 102 at this time. Left/right clutch 102, therefore, is energized and couples gear 96 to shaft 98, FIG. 4. With shaft 98 and gear 96 coupled, motor drive shaft 90 drives carriage 74 in the direction D', as already explained, and frame 24 scans the first row of the array.

At this time, movable contact 318a is not connected to contact 318b so that contact 318b is disconnected from line 316. Consequently, no current flows to up-/down clutch 118 through contact 318b and clutch 118 is de-energized. When up/down clutch 118 is de-energized, gear 116 is not coupled to shaft 18, FIG. 4. Therefore, as motor drive shaft 90 drives shaft 98, drum 10 traverses cable 106 in the direction D', frame 24 scans the first row of the array in the direction D', and holder 13 and sampling element 99 remain in a non-sampling or uppermost position.

Frame 24 continuously scans a row in the direction D', stopping at a preselected position in the row only after roller 56 of program switch 46 contacts the annular head 52 of a cam 44 depressed in accordance with the program. When roller 56 contacts annular head 52, FIG. 13, leaf spring 54 is depressed against actuator 46a, causing movable contact 46d, FIG. 14B, to break connection with contact 46c and make connection with contact 46b. At this time, current flows from contact 46b to coil 320 and coil 320 is energized. Movable contact 318a, therefore, breaks connection with contact 318c and makes connection with contact 318b. Consequently, current flows through contact 318b to up/down clutch 118 and clutch 118 is energized. At the same time, no current flows through contact 318c to left/right clutch 102. However, diode $D_1$ conducts current from contact 46b to left/right clutch 102 and clutch 102 remains energized. Therefore, left/right clutch 102 continues to couple gear 96 to shaft 98, FIG. 4, while up/down clutch 118 couples gear 116 to shaft 18. Carriage 74, therefore, continues to move in the direction D' while shaft 90 starts to drive shaft 18 and gear 22. Gear 22 starts to drive rack 20 downwardly in the direction B, lowering holder 13 and sampling element 99 in the direction B towards a sampling or lowermost position at which material is to be inspected or transferred.

Figure 12:
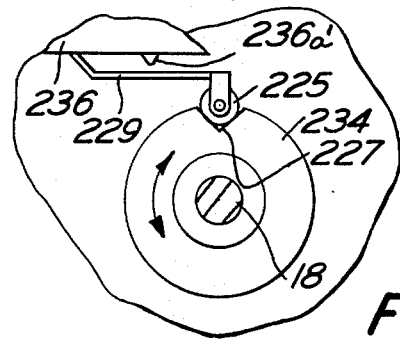
FIG. 12 is a view in cross-section taken along the lines 11—11 in FIG. 4 showing the operational state of the apparatus in FIG. 4 while material is being inspected or transferred at a position in the array.
Figure 14B:
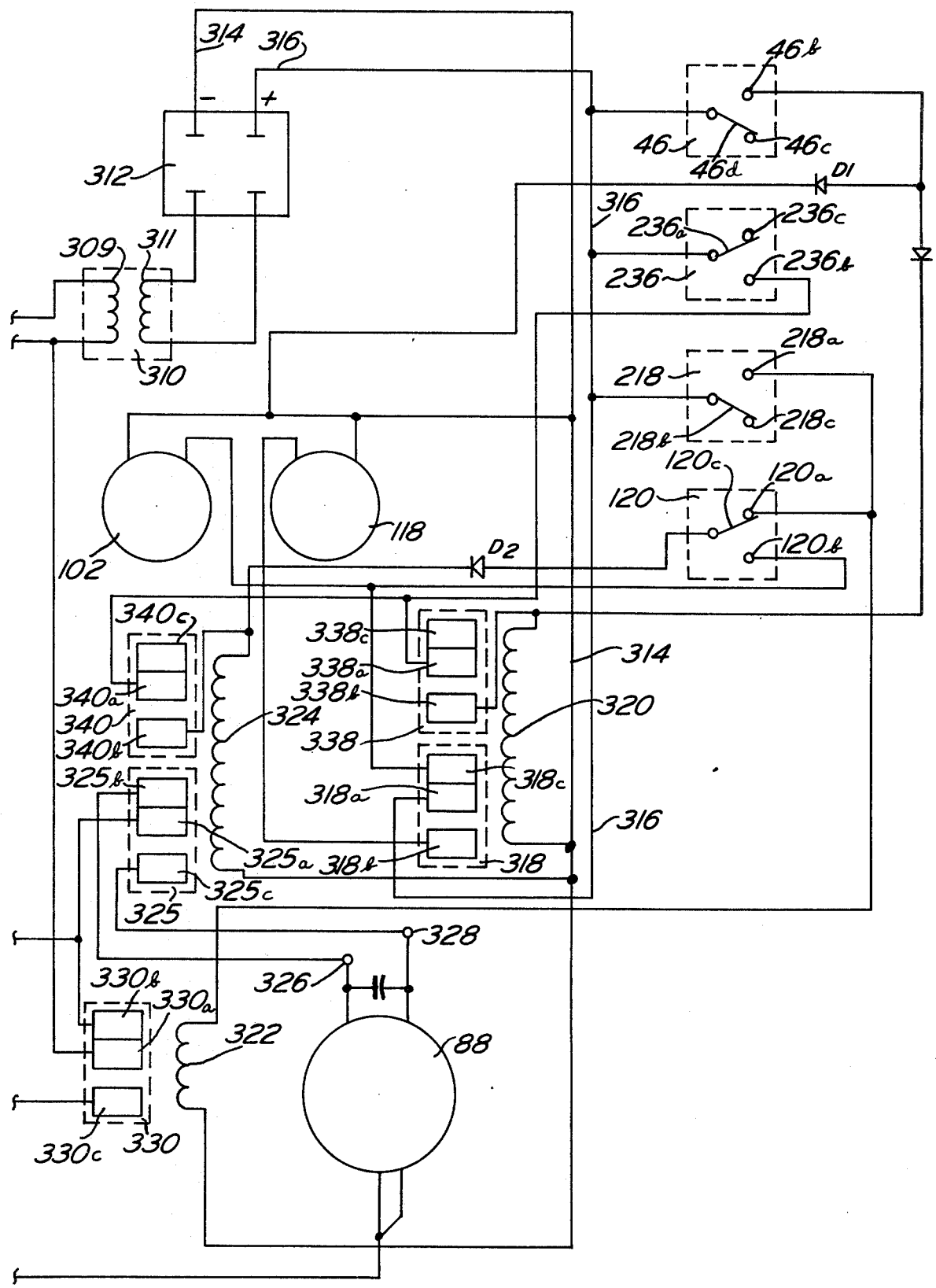

When holder 13 and sampling element 99 are in the nonsampling position, roller 225, FIG. 12, is lodged in a notch 227 in camming wheel 234, and spring-loaded ball 103, FIG. 10, is seated in notch 105 in gear 22. Camming wheel 234 is securely mounted on shaft 18, FIG. 4. Roller 225, FIG. 12, is pivotally connected to a leaf spring 229 in top sensing switch 236. When roller 225 is lodged in notch 227, movable contact 236a remains connected to contact 236c. However, when shaft 18 begins to rotate, it dislodges roller 225 from notch 227 and camming wheel 234 rollably contacts roller 225, causing leaf spring 229 to mechanically contact actuator 236a'. Actuator 236a' causes movable contact 236a, FIG. 14B, to make connection with contact 236b. The line 316 voltage, therefore, FIG. 14B, is transmitted through contact 236b to movable contacts 340a and 338a. At this time, coil 320 is still energized while coils 322 and 324 are de-energized. Coils 322 and 324 control contacts 330, 325 and 340. Therefore, movable contact 338a is connected to contact 338b, thereby supplying an additional current path to coil 320 from line 316, while movable contact 340a remains connected to contact 340c, movable contact 325a remains connected to contact 325b, and movable contact 330a remains connected to contact 330b. Current, therefore, continues to flow to terminal 326 of the motor field winding through contacts 330a, 330b, 325a and 325b. Motor drive shaft 90, then, continues to rotate, driving holder 13 downwardly in the direction B, FIG. 4.

As mentioned previously, left/right clutch 102 is still energized after roller 56 initially contacts annular head 52. Therefore, carriage 74 continues to move in the direction D', moving roller 56 past annular head 52. When roller 56 releases from rollable contact with head 52, movable contact 46d returns to connection with contact 46c, disconnecting line 316 from contact 46b and coil 320. However, coil 320 is not de-energized at the time since movable contact 338a continues to supply current from contact 236b to contact 338b and coil 320. As a result, coil 320 and up/down clutch 118 remain energized. Additionally, at this time, diode $D_1$ is no longer connected to line 316 by contact 36b so that left/right clutch 102 is now de-energized. Accordingly, carriage 74 stops while shaft 90, FIG. 4, continues to drive holder 13 and sampling element 99 in the direction B towards the sampling position. It should be appreciated that carriage 74 moves only for a relatively brief period of time while holder 13 and sampling element 99 are driven towards the preselected position since roller 56 only briefly contacts annular head 52.

Figure 11:
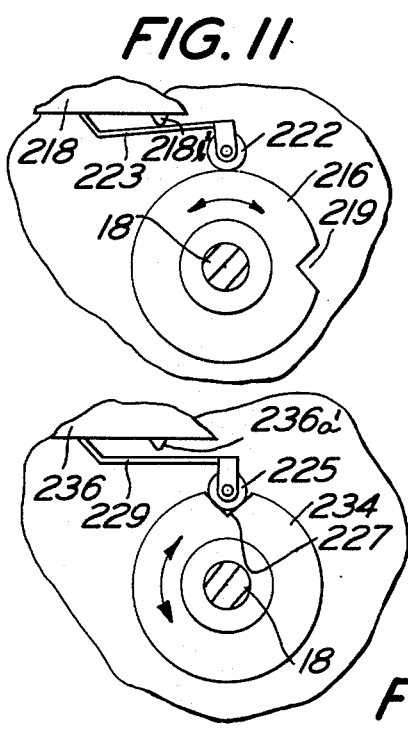
FIG. 11 is a view in cross-section taken along the lines 11—11 in FIG. 4 showing the operational state of the apparatus in FIG. 4 when material is not being inspected or transferred at a position in the array.

Before holder 13 and sampling element 99 reach the sampling or lowermost position, that is, the position at which material is to be inspected or transferred, roller 222 rollably contacts camming wheel 216, FIG. 11. Camming wheel 216 is securely mounted on shaft 18, FIG. 4. Roller 222 is pivotally connected to a leaf spring 223 which mechanically contacts actuator 218b', causing movable contact 218b, FIG. 14B, to make connection with 218c when roller 222 rollably contacts camming wheel 216. When holder 13 reaches its lowermost position, roller 222, FIG. 11, lodges in notch 219 and leaf spring 223 releases from mechanical contact with actuator 218b'. Therefore, movable contact 218b, FIG. 14B, makes connection with contact 218a, energizing coils 322 and 324. With coil 324 energized, movable contact 325a breaks connection with contact 325b and makes connection with contact 325c, and movable contact 340a makes connection with contact 340b, providing an additional current path to coil 324. With coil 322 energized, movable contact 330a breaks connection with contact 330b and makes connection with contact 330c. With holder 13 in its lowermost position, after a predetermined time delay $T_0$, the alternating current flowing through primary coil 309 flows through contacts 325a and 325c to terminal 328 rather than terminal 326, thereby reversing the flow of current to the motor field winding. Consequently, motor drive shaft 90, FIG. 4, reverses its direction of rotation, in turn causing shaft 18 to reverse its direction of rotation. Gear 22, therefore, starts to drive rack 20 upwardly in the direction B'.

During the time delay interval $T_0$, material is inspected or transferred by sampling element 99 while holder 13 remains in its lowermost position. For example, during time interval $T_0$, a pump (not shown) controlled by pump control circuit 336, FIG. 14A, may be connected by conventional means to sampling element 99 to transfer a predetermined quantity of material through sampling element 99 to or from a container at the preselected position. Pump control circuit 336 will be described in detail hereinafter. To prevent alternating current from flowing to the motor field winding during time interval $T_0$, that is, to prevent drive shaft 90 from rotating until time interval $T_0$ expires, coil 334 remains de-energized, FIG. 14A. With coil 334 de-energized, contacts 332a and 332c do not make connection and no current flows from contacts 330a and 330c to the motor field winding terminals 326 or 328. Consequently, the motor 88 remains stopped during time interval $T_0$.

Referring to FIG. 14A, there is shown within dashed lines a pump control circuit 336 which supplies an a-c voltage at terminals 500 and 502 for driving a pump (not shown) during time interval $T_0$. The circuit is controlled by an adjustable timer motor 300 which, in the preferred embodiment, is a conventional 30-second timer motor. The circuit may be used in either an automatic mode in conjunction with a printer (not shown) connected across terminals 506 and 508, or a semi-automatic mode. In the semi-automatic mode, operation is controlled by a foot switch 504 which is normally open.

In the automatic mode, before holder 13 has reached its lowermost position with carriage 74 stopped, contacts 512 and 514 are open, disconnecting terminal 502 from the a-c source. Therefore, no current flows through coil 334, FIG. 14A, and the coil is de-energized. Prior to automatic operation of the machine, timer motor 300 is set to the desired time interval for operating the pump. Until current flows through coil 334, contacts 332a and 332b remain connected and no current flows to the motor field winding. When holder 13 reaches its lowermost position, coil 322 is energized and current flows through contacts 330a and 330c to coil 532. Coil 532 controls contacts 514. Current flowing through coil 532 causes contacts 514 to close, and current flows through coil 510 and contacts 514 and 516. Coil 510 controls contacts 512 so that contacts 512 also close at this time, connecting terminal 502 through contacts 516 to the a-c source independently of contacts 514. At the same time, current flows though timer motor 300, and the timer motor begins to time out.

Timer motor 300 controls contacts 518 and 520. Before timer motor 300 times out, contacts 520 are closed and contacts 518 are open. Therefore, when holder 13 reaches its lowermost position, terminal 502 is connected through contacts 514 and 516 to one line of the a-c source, and terminal 500 is connected through contacts 520 to the other a-c line. Accordingly, an alternating voltage appears between terminals 500 and 502 to drive the pump. The pump, then, transfers material through sampling element 99 either to or from the container, depending on the mode of operation of the pump. During this time, coil 334 remains de-energized since contacts 518 are open and SCR 526 cannot fire.

With coil 334 de-energized, contacts 332a and 332c are disconnected, no current flows to motor 88, and holder 13 remains in its lowermost position. When timer motor 300 times out, contacts 520 open and contacts 518 close, disconnecting terminal 500 from the a-c source and causing the pump to stop. Capacitor $C_2$ provides a d-c voltage across terminals 522 and 524, and capacitor $C_1$ charges to this d-c voltage through resistors $R_1$ and $R_2$. Resistor $R_1$ is a variable resistor fior adjusting the time constant of the charging circuit, $R_1$, $R_2$ and $C_1$. Capacitor $C_1$ is connected to the emitter of UJT 528. When the emitter reaches the emitter peak point voltage, UJT 528 turns on, generating a pulse across resistor $R_4$. Resistor $R_4$ is connected to the gate of SCR 526 and, when UJT 528 turns on, SCR 526 fires, causing current to flow in coil 334. Coil 334 controls contacts 516, 332 and 530. Consequently, when current flows through coil 334, movable contact 332a connects with contact 332c, causing current to flow to the field winding of motor 88 at terminal 328 and causing coil 532 to become de-energized, thereby opening contacts 514; contacts 516 open to disconnect terminal 502 from the a-c source, causing current to stop flowing through coil 510, thereby opening contacts 512; and contacts 530 close to activate the printer which prints the output of a spectrophotometer or other device used to analyze the material inspected in or withdrawn from the container.

In the semi-automatic mode, coil 532 is disconnected from contact 332b and the a-c source, and contacts 514 are removed from circuit 336. Foot switch 504 is momentarily depressed to initiate current flow through coil 510 when holder 13 reaches its lowermost position, and operation of pump circuit 336 is otherwise identical to the automatic mode.

A typical set of components for pump circuit 336 is given below in Table 1.

TABLE 1

| Capacitors | Resistors | UJT | SCR |
|---|---|---|---|
| $C_1$ 25µf, 25v | $R_1$ 1M | 2N4852 | C106B |
| $C_2$ 200µf, 150v | $R_2$ 100K | | |
| | $R_3$ 56K, 1w | | |
| | $R_4$ 100 | | |
| | $R_5$ 100 | | |

When time interval $T_0$ expires, current flows through coil 334, causing movable contact 332a to break connection with contact 332b and make connection with contact 332c. The alternating current, therefore, flows through contacts 330a, 330c, 332a, 332c and 325a and 325c to terminal 328 rather than terminal 326. The current in the motor field winding, therefore, reverses direction, causing shaft 90 to reverse its direction of rotation. Therefore, when time interval $T_0$ expires, shaft 18 follows motor drive shaft 90 and reverses its direction of rotation, causing gear 22 to drive rack 20 upwardly in the direction B', FIG. 4.

In addition, at the expiration of interval $T_0$, roller 222, FIG. 11, is dislodged from notch 219 as shaft 18 resumes rotation. Therefore, actuator 218b' causes movable contact 218b, FIG. 14B, to return to connection with contact 218c. Contact 236b continues to supply a current path to contacts 340a and 340b which are connected to coil 324 and, through carriage direction switch 120 and diode D2, to coil 322. Therefore, coil 324 remains energized and diode D2 prevents coil 322 from being energized. As a reuslt, alternating current continues to flow through contacts 330a and 330c, 332a and 332c, and 325a and 325c to terminal 328 of motor 88 and shaft 18, FIG. 4, drives rack 20 upwardly in the direction B'.

As shaft 18 rotates, roller 225 rollably contacts camming wheel 234 until the roller lodges in notch 227, FIG. 12. At this time, holder 13 returns to the uppermost or non-sampling position. With roller 225 lodged in notch 227, actuator 236a' causes movable contact 236a, FIG. 14B, to break connection with contact 236b and returns to connection with contact 236c. As a result, no current flows from contact 236b to contacts 340a and 338a and coils 320 and 324 are de-energized. Therefore, movable contact 388a makes connection with contact 338c, movable contact 318a makes connection with 318c, movable contact 330a makes connection with contact 330b, movable contact 325a makes connection with contact 325b, and movable contact 340a makes connection with 340c. Accordingly, alternating current now flows through contacts 330a and 330b and 325a and 325b to terminal 326 of the motor field winding. The current in the motor field winding, therefore, again reverses direction, causing motor drive shaft 90 once more to reverse its direction of rotation.

As already mentioned, when movable contact 236a makes connection with contact 236c, coil 320 is de-energized and movable contact 318a breaks connection with contact 318b and makes connection with contact 318c. Consequently, current flows from line 316 through movable contact 318a to contact 318c and left/right clutch 102. Left/right clutch 102, then, is energized and it re-couples gear 96 to shaft 98. At the same time, however, up/down clutch 118 no longer receives current through contact 318b/ Up/down clutch 118, then, is de-energized and it de-couples gear 116 from shaft 18. Holder 13, therefore, remains in its uppermost position, and drive shaft 90 resumes rotation in the direction which causes drum 104 to traverse cable 106 in the direction D'. Consequently, carriage 74 resumes motion in the direction D' and continues to scan the remainder of containers in the row.

If other cams 44 are depressed in accordance with the program, program switch 46, bottom sensing switch 218 and top sensing switch 236 cause carriage 74 to stop at preselected positions determined by these cams and material is inspected or transferred by sampling element 99 at each preselected position as described above.

After carriage 74 scans the last column position in the first row, rod 124, FIG. 3, contacts actuator 120c', causing movable contact 120c, FIG. 14B, to break connection with contact 120a and make connection with contact 120b. Coil 324 is thereby connected through contacts 318c and 318a to line 316. Therefore, current flows through coil 324, causing movable contact 340a to make connection with contact 340b and movable contact 325a to make connection with contact 325c. Accordingly, alternating current now flows through contacts 330a and 330b to contacts 325a and 325c and to terminal 328 of motor 88. Consequently, the direction of current in the motor field winding reverses, causing drive shaft 90 to reverse its direction of rotation. Carriage 74, then, travels back to the first column position in the direction D.

When carriage 74 reaches the first column position, rod 122 contacts actuator 120c', causing movable contact 120c, FIG. 14B, to break connection with contact 120b and to re-make connection with contact 120a. Consequently, coil 324 is de-energized, movable contact 325a makes connection with contact 325b, and current flows to terminal 326 of motor 88, that is, the direction of current flow in the motor field winding again reverses. Accordingly, motor drive shaft 90 again reverses its direction of rotation, causing drum 104 to traverse cable 106 in the direction D' with frame 24 aligned with the next row to be scanned. The operation of the apparatus, described above, is repeated for each successive row which is to be scanned.

As already explained in detail, when shaft 26 has been fully extended, rod 198 operates switch 200 to cut off power to the machine. Specifically, rod 198 contacts actuator 200a, FIG. 2, causing movable contact 200d, FIG. 14A, to break connection with contact 200b and to make connection with 200c. At this time, operate switch 173 is not depressed, and movable contact 173a does not make contact with contact 173b. Therefore, when movable contact 200d breaks connection with contact 200b, no current flows to coils 179 and 309. Therefore, no current flows to motor 88 and the apparatus shuts off. Frame 24 can now be aligned with the first row of the next array to be scanned, as explained in detail in the preceding description of the mechanical structure of the present invention, and the automatic operation of the apparatus can be repeated for the next array.

In operation, frame 24 is aligned with the first row to be scanned in the array by sliding rod 26 through bushing 176 and aperture 67, FIG. 4. Handle 40, FIG. 1, is locked into position in slot 42 to enable guide rail 34 and block 28 to extend rod 26 a length equal to the distance between adjacent predetermined rows of the array. Those cams 44, FIG. 13, which coincide with column positions in the array at which material is to be sampled are depressed. The entire series of cams 44, including those depressed and not depressed, and the position of handle 40 in slot 42 determine the scanning program which the machine will follow during automatic operation. Power on switch 171, FIG. 14A, and operate switch 173 are then depressed in sequence to turn on motor 88, that is, to initiate automatic operation of the machine. Motor 88 drives drum 104 along cable 106 in the direction D', and frame 24, holder 13 and sampling element 99 scan the first row of the array. Frame 24, holder 13 and sampling element travel in the direction D' during the scan until roller 56 of program switch 46 contacts the annular head 52 of a cam 44 which has been depressed in accordance with the program. Program switch 46, when operated by a depressed cam 44, actuates up/down clutch 118 to couple drive shaft 90 to shaft 18. Therefore, shaft 18 begins to rotate and carriage 74 continues to move in the direction D'. As shaft 18 begins to rotate, camming wheel 234 actuates switch 236. Carriage 74 continues briefly to move in the direction D', until roller 56 releases from contact with annular head 52, thereby de-activating program switch 46 and causing left/right clutch 102 to become de-energized. With left/right clutch 102 de-energized, shaft 98 is de-coupled from drive shaft 90 and carriage 74 stops. Shaft 18, however, continues to rotate, driving gear 22 which is located in frame 24. Gear 22, in turn, drives rack 20 downwardly in the direction B, causing holder 13 and sampling element 99 to travel to a lowermost or sampling position at the column position aligned with cam 44.

When rotation of shaft 18 causes holder 13 to reach the lowermost position, camming wheel 216 operates switch 218, causing clutch 118 to de-couple shaft 18 from motor drive shaft 90. Holder 13 remains in the lowermost position for a predetermined time $T_O$ until timer 300 times out and coil 334 becomes energized. During this time, pump circuit 336 operates a pump which causes material to be transferred through the sampling element 99 locked in holder 13 to or from the preselected column position. Alternatively, material at the preselected column position may be inspected by the sampling element 99 in response to any conventional component connected to circuit 336, FIG. 14A. Thus, the particular function of the sampling element, e.g., to inspect or to transfer material, is initiated in response to conventional components connected to terminals 500 and 502, FIG. 14A. For instance, the sampling element may inspect the material at the preselected column position in cooperation with a spectrophotometer or other device connected to terminals 500 and 502.

When coil 334 is energized it causes motor drive shaft 90 to reverse its direction of rotation. Drive shaft 90 then causes shaft 18 and gear 22 to drive rack 20 upwardly in the direction B', away from the preselected position at which material has just been sampled. When holder 13 and sampling element 99 reach the nonsampling or uppermost position, camming wheel 234, FIG. 17, deactivates top sensing switch 236, causing up-/down clutch 118 to decouple shaft 18 from drive shaft 90, and spring-loaded ball 103, FIG. 10, enters notch 105 in gear 22, keeping holder 13 in the uppermost position. Thus, with shafts 18 and 90 de-coupled, holder 13 remains in its uppermost position. When deactivated, top sensing switch 236, FIG. 14B, also causes motor drive shaft 90 to again reverse its direction of rotation and left/right clutch 102 to recouple shaft 98 to drive shaft 90. As a result, shaft 98 again drives drum 104, FIG. 4, along cable 106 and carriage 74 resumes motion in the direction D' until roller 56 contacts the next cam 44 which has been depressed according to the program. The sequence of automatic operations previously described is then repeated.

After the entire first row has been scanned, rod 124, FIG. 3, operates carriage direction switch 120 which reverses the direction of rotation of motor drive shaft 90, causing the direction of rotation of shaft 98 and drum 104 to reverse. During the scan of the first row, guide rail 34 causes block 28, FIG. 2, to slide along rod 132 in the direction C' into contact with rod 186 of block 174, causing block 174 to slide in the direction C' along bushing 176. At the end of the first scan, block 28 has caused block 174 to slide far enough along bushing 176 so that notch 196 in latch 188, FIG. 5, engages rod 170. With rod 170 engaged in notch 196, finger 140, FIG. 8, contacts rod 26 under the biasing force of spring 148. Finger 140, then, lodges in notch 32 on rod 26. As drum 104 traverses cable 106 in the direction D, that is, as carriage 74 returns to the first column position, guide rail 34 causes block 28 to slide along rod 132 in the direction C, FIG. 2. As block 28 slides along rod 132 in the direction C, finger 140 extends a predetermined length of rod 26 in the direction C. The predetermined length is fixed by the initial location of guide rail 34. Frame 24, therefore, is displaced simultaneously in the direction D and C, FIG. 1. Consequently, frame 24 travels along path R to the first column position of the next row to be scanned. Rod 122, FIG. 3, then operates carriage direction switch 120 which again reverses the direction of rotation of motor drive shaft 90, FIG. 4, causing carriage 74 to again move in direction D'. The sequence of events described above is repeated for each row in the array.

Upon completing the scan of the last row of the array drum 104 reverses its direction of rotation, causing carriage 74 to return to the first column position. As carriage 74 returns to the first column position following the scan of the last row, finger 140 extends the last portion of rod 26. As the last portion of rod 26 is extended, latch 188, FIG. 5, is urged upwardly by rod 198 to release rod 170 from notch 196. When rod 170 is released from notch 196, spring 178 causes block 174, FIG. 4, to move forward and rod 170 contacts register plate 160, FIG. 7. When contacted by rod 170, register plate 160 depresses flange 142, causing finger 140 to rotate away from rod 26. In addition, rod 198 operates switch 200 which cuts off the power to motor 88. Therefore, when the carriage 74 has returned to the first column position following the scan of the last predetermined row in the array, rod 26 can be freely moved, without contacting finger 140, to align frame 24 with the first row of the next array to be scanned.

In the preferred embodiment of the invention described herein, material to be inspected or transferred at preselected positions in a rectangular array may be inspected in or transferred to or from containers located at the preselected positions. It should be obvious, however, that the invention can also be used in other applications. For example, the sampling element 99 may be an electro-optical device or other sensing element for detecting printed or embossed matter on paper or other matter, line by line. The invention is particularly suited for such application since it scans each line only in one direction, which is the natural pattern for reading alphanumeric characters.

The present invention may be embodied in other specific forms without departing from the spirit or essential attributes thereof and, accordingly, reference should be made to the appended claims, rather than to the foregoing specification as indicating the scope of the invention.

I claim:

1. Apparatus for scanning positions arranged in a rectangular array of columns and rows according to a predetermined program, comprising:

means for sampling material at said positions;

means for transporting said sampling means in the same direction along one or more predetermined rows of said positions according to said predetermined program;

means for selectively stopping said sampling means at one or more preselected positions in said predetermined rows according to said predetermined program; and means responsive to said selectively stopping means for causing said sampling means to sample said material at each of said preselected positions according to said predetermined program.

2. Apparatus according to claim 1 including means for automatically stopping said sampling means after said sampling means has been transported across every predetermined row of the rectangular array.

3. Apparatus according to claim 1 wherein said means for transporting includes means for transporting said sampling means from the last column position of each of said predetermined rows to the first column position of the next predetermined row.

4. Apparatus according to claim 1 wherein said causing means includes means for reciprocally transporting said sampling means from a non-sampling position to a sampling position at which said material is sampled.

5. Apparatus according to claim 4 including means responsive to said reciprocally transporting means for selectively transferring material through said sampling means to or from said preselected position while said sampling means is at said sampling position.

6. Apparatus according to claim 1 wherein said sampling means includes an element for inspecting said material.

7. Apparatus according to claim 1 wherein said sampling means includes a transfer tube for conducting material to or from said preselected positions.

8. Apparatus according to claim 1 wherein said means for selectively stopping includes means for stopping said sampling means at each of said preselected positions for a predetermined interval of time.

9. Apparatus for scanning, with a sampling element, positions arranged in a rectangular array of columns and rows according to a predetermined program, comprising:

a casing;

guide means secured to said casing;

a carriage slidably mounted on said guide means;

first means for driving said carriage alternatingly in first and second directions on said guide means;

a holder for supporting said sampling element, said holder being mechanically coupled to said carriage for movement with said carriage in said first and second direction;

means for selectively stopping said carriage from moving in said first direction only when said holder reaches one or more preselected positions in one or more predetermined rows of said array;

means for activating said sampling element when said carriage is stopped; and second means for driving said holder from one of said predetermined rows to a next predetermined row as said first driving means drives said carriage in said second direction only.

10. Apparatus according to claim 9 wherein said first driving means includes a motor mounted on said carriage, a first shaft rotatably mounted on said carriage and selectively coupled to said motor, said first shaft being provided with a drum, and a cable wrapped around said drum and connected to said casing.

11. Apparatus according to claim 9 wherein said activating means includes means for reciprocally transporting said sampling element from an uppermost position to a lowermost position at which said sampling element is activated.

12. Apparatus according to claim 11 wherein said reciprocally transporting means includes a second shaft rotatably connected to said holder, said second shaft being slidably mounted on said carriage and selectively coupled to said motor.

13. Apparatus according to claim 12 wherein said second driving means includes a notched rod slidably mounted on said carriage and securely fastened to said holder, a support rod, said support rod being securely mounted on said carriage, a block slidably mounted on said support rod, said block having a pivotable member, means for driving said block reciprocally on said support rod in synchronization with movement of said carriage, and means for causing said block pivotable member to lodge in one notch of said notched rod when said block travels in one direction and to pass over said notched rod when said block travels in the opposite direction.

14. Apparatus according to claim 13 wherein said causing means includes a register plate pivotably mounted on said carriage, means for pivoting said register plate to contact said block pivotable member, whereby said block pivotable member pivots away from said notched rod and passes over said rod notches.

15. Apparatus according to claim 10 wherein said means for selectively stopping said carriage includes a plurality of cams mounted on said casing and a program switch mounted on said carriage for causing said first shaft and said motor to de-couple subsequent to said program switch contacting one of said cams.

16. Apparatus for scanning positions arranged in a rectangular array of columns and rows with an element for sampling said positions according to a predetermined program, comprising:

means for transporting said element in the same direction along one or more predetermined rows of positions; and means for temporarily stopping said element at one or more of said positions in said predetermined rows in accordance with said predetermined program.

17. Apparatus according to claim 16 including means for activating said element when said element is stopped.

18. Apparatus for scanning a plurality of row and column positions with a sensing element according to a predetermined program, comprising:

means for transporting said sensing element in the same direction along one or more predetermined rows of said positions; and means for temporarily stopping said sensing element at one or more preselected positions in said predetermined rows in accordance with said predetermined program.

19. Apparatus according to claim 18 including means for transporting said sensing element from the last column position of each of said predetermined rows to the first column position of the next predetermined row.

20. A method for automatically scanning positions arranged in a rectangular array of columns and rows with a sampling element according to a predetermined program, comprising:

transporting said sampling element in the same direction along one or more predetermined rows of said positions;

selectively stopping said sampling element at one or more of said positions in said predetermined rows according to said predetermined program; and activating said sampling element when said sampling element is stopped.

21. A method according to claim 20 including automatically stopping said sampling element after said sampling element has been transported across every predetermined row of said array of positions.

22. A method for automatically scanning containers arranged in a rectangular array of columns and rows with a sampling element, comprising:

transporting said sampling element in the same direction along one or more predetermined rows of containers; and temporarily stopping said element at one or more of said containers in said predetermined rows in accordance with said predetermined program.

23. A method for automatically scanning a plurality of row and column positions with a sensing element according to a predetermined program, comprising:

continuously transporting said sensing element in the same direction along one or more predetermined rows of said positions; and temporarily stopping said element at one or more of said positions in said predetermined rows in accordance with said predetermined program.

* * * * *